United States Patent [19]
Hirako

[11] Patent Number: 5,155,543
[45] Date of Patent: Oct. 13, 1992

[54] ADJUSTABLE FLOW CYTOMETER

[75] Inventor: Shinichi Hirako, Nagaokakyo, Japan

[73] Assignee: Omron Corporation, Kyoto, Japan

[21] Appl. No.: 570,631

[22] Filed: Aug. 22, 1990

[30] Foreign Application Priority Data

Aug. 22, 1989 [JP] Japan ............................ 1-97576[U]

[51] Int. Cl.$^5$ ............................................. G01N 21/53
[52] U.S. Cl. ...................................... 356/73; 356/343
[58] Field of Search ................... 356/73, 336, 338, 343

[56] References Cited

U.S. PATENT DOCUMENTS

| | | | |
|---|---|---|---|
| 4,318,481 | 3/1982 | Lombardo et al. | 209/3.1 |
| 4,318,483 | 3/1982 | Lombardo et al. | 209/3.1 |
| 4,765,737 | 8/1988 | Harris et al. | 356/73 |

*Primary Examiner*—Vincent P. McGraw
*Assistant Examiner*—LaCharles P. Keesee

[57] ABSTRACT

A flow cytometer has a flow cell containing a flowing stream of a number of particles which flow one at a time in a straight line based on hydrodynamic methods, a radiator for radiating a light on the particles flowing through the flow cell, a forward scattered light detector for detecting light scattered in the same direction as the radiating light, and a right angle signal light detector for detecting light radiated in a right angle with respect to the direction of the radiating light. The flow cell and the forward scattered light detector are contained in a single mount, and the mount is supported on a bench through an adjusting mechanism. In this way, the flow cell and the forward scattered light detector can be adjusted without disturbing their locations relative to each other.

11 Claims, 5 Drawing Sheets

ADJUSTABLE FLOW CYTOMETER

FIELD OF INVENTION

This invention relates to a flow cytometer which analyzes a cell-like particle. More specifically, this invention relates to an adjustment mechanism for a light axis in such a flow cytometer.

REFERENCE TO RELATED APPLICATION

The subject matter of this application is related to the subject matter disclosed and claimed in commonly assigned U.S. application Ser. No. 07/570,629, filed Aug. 22, 1990.

BACKGROUND OF THE INVENTION

Conventional flow cytometers cause a number of particles such as cells to flow in a straight line in aqueous suspension. These particles are analyzed using a hydrodynamic method, whereby light is radiated onto particles flowing through a flow channel, thereby detecting the scattered light and fluorescent light from the particles and converting it to electronic signals for analysis. An important feature of the flow cytometer makes it possible to quickly analyze many particles at one time.

In FIGS. 4 and 5, such a conventional flow cytometer is shown.

Flow cell 34 has a flow channel 34a which has a sheath liquid together with particles subject to analysis flowing therethrough. In the flow channel 34a, a number of particles move through in a straight line caused by flowing of a sheath liquid based on a hydrodynamic method. Mount 32 supports flow cell 34 and is mounted to a bench 31 through adjusting mechanism 33. The flow cell 34 is movable in the x and y directions by adjusting screws 33x and 33y of the adjusting mechanism 33 respectively. Light focusing lens 44 focuses a beam L0 from a laser (not shown) onto particles traveling through the flow channel 34a of the flow cell 34, thereby causing the particles to radiate two types of light, namely scattered light and fluorescent light.

A forward scattering light detecting assembly 35 is located in the forward direction of the beam L0 (x-axis direction). The light detecting assembly 35 includes mount 43, light path tube 36, lens 37, and a light detector container 39. Light path tube 36 is supported by mount 43. One end of light path tube 36 close to flow cell 34 has lens 37 while the other end is close to light detector container 39. In light detector container 39, pinhole 40 and light detector 41 are contained. Pinhole 40 together with light detector 41 are movable in the y and z axes by means of adjustment screws 39y and 39z respectively. Scattered light L1 produced from particles collected through lens 37, with its background light or noise eliminated through pinhole 40, is finally received by light detector 41 and converted into electronic signals. Beam blocker 42 prevents beam L0 from getting into light detector 41.

A right angle light detecting assembly 45 is disposed in the right angle direction (y-axis) with respect to the propagating direction of beam L0. The right angle light detecting assembly 45 includes light path tube 46, lenses 47a and 47b, light detector container 49 and so on. Lenses 47a and 47b are disposed at one end of light path tube 46, while its other end is inserted into detector container 49. In light detector container 49, pinhole 50 and light detector 51 are disposed. Light L2 produced from particles collected through lenses 47a and 47b, with background noises eliminated through pinhole 50, is then received by light detector 51 and converted into electronic signals.

In conventional flow cytometers, flow cell 34 and forward light scattering detector 35 must be separately adjusted which takes much time to complete, especially when light axis lo of light beam L0 is not in line with light axis m of the forward scattering light detecting assembly 35. FIG. 3 shows a detailed depiction of these problems. In general, light beam L0 is a bell curve with a center light axis lo. Accordingly, if a particle p is on the light axis lo, the most intensified forward scattered light is received. Referring to FIG. 3c, a particle p flowing through a center of flow channel 34a is on both the light axis lo and light axis m of the forward scattered light detecting assembly 35, thereby showing the most optimal condition with light axis lo in line with axis m. On the contrary, in FIG. 3a, light axis lo is not in line with light axis m. Particle p is located on light axis m but light axis lo is not in line with particle p. In this case, flow cell 34 must be moved in the y-axis plus direction using adjustment screw 33y. So, when flow cell 34 is moved in the y-axis plus direction in order to locate the particle p on the light axis lo, the particle p is deviated from light axis m which means the focusing point Q of the forward scattered light L1 is also deviated from light axis m, thereby reducing the amount of light entering light detector 41 and lowering output signals as shown in FIG. 3b. Accordingly, adjustment screw 39y is operated to move pinhole 40 and light detector 41 in the y-axis minus direction.

However, if flow cell 34 is moved erroneously in the y-axis minus direction as in FIG. 3a, the light intensity received by the particle p decreases, thereby leading to a reduction of the output signals of light detector 41. For this reason, it is very difficult to judge whether flow cell 34 correctly moved based on the output signal of light detector 41. Therefore, in the actual practical light axis adjustment of flow cell 34, the slight movement of pinhole 40 and light detector 41 must be repeated to raise the output signal of light detector 41 every time flow cell 34 is slightly moved, so that light axis lo and light axis m are kept in line with each other. In addition, the width of light beam L0 and flow channel 21a is generally less than 0.2 millimeters, thereby requiring skillful manipulation of pinhole 40 and light detector 41 for light axis adjustment.

SUMMARY OF THE INVENTION

In view of the above, it is an overall object of the present invention, among others, to provide a flow cytometer with an easily adjustable light axis.

In order to achieve this object, the present invention is characterized in that flow cell and forward scattered light detecting assembly are adjusted integrally together. For this reason, once the locational relationship between the flow cell and the forward scattering light detecting assembly have been adjusted, the locational relationship will continue to be maintained even if the location of the flow cell is subsequently adjusted by moving the mount. Accordingly, the adjustment of the light axis can be made easily and quickly by referring to the output signal of the light detector.

DETAILED DESCRIPTION OF THE INVENTION

Figure 1:
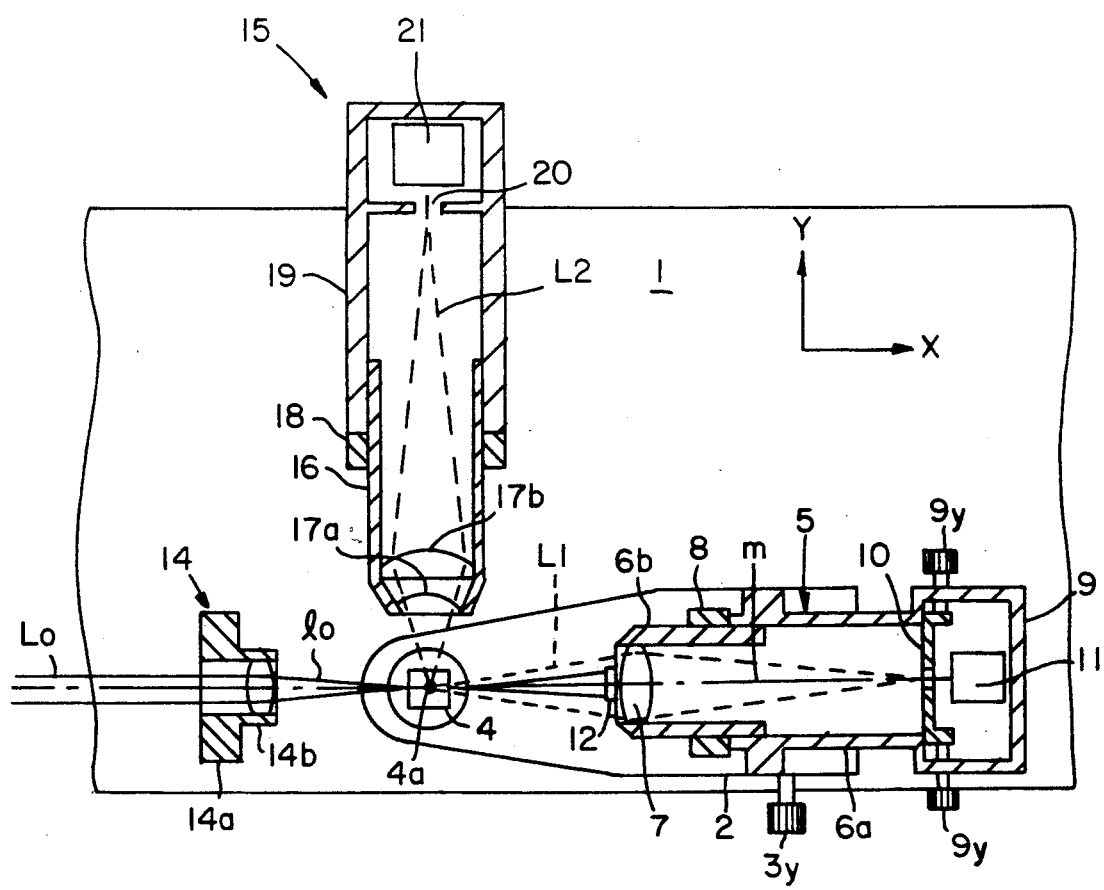
FIG. 1 is a plan view of the flow cytometer of this invention, a part of which is a cross section.
Figure 2:
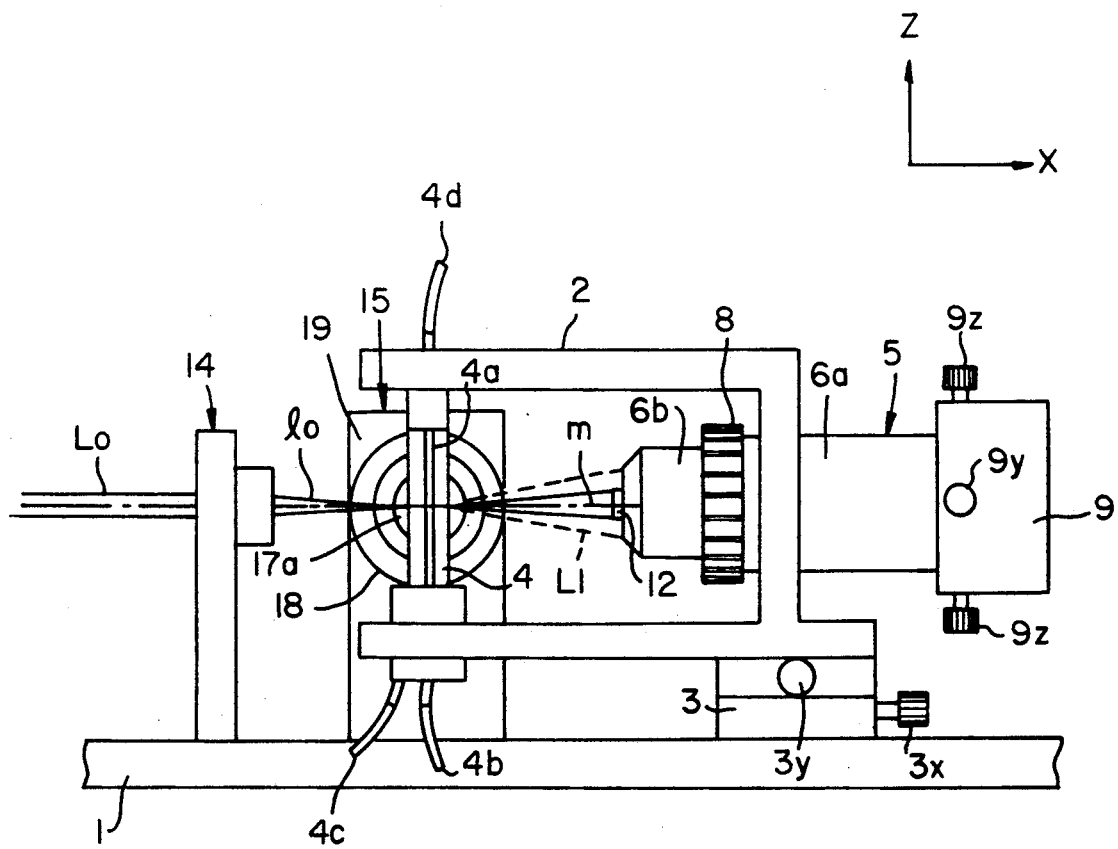
FIG. 2 is a side view of the optical portion of the flow cytometer shown in FIG. 1, FIG. 3a, 3b, and 3c are views illustrating the way the light axis is adjusted with respect to an embodiment of this invention as well as in accordance with the prior art.
Figure 3A:
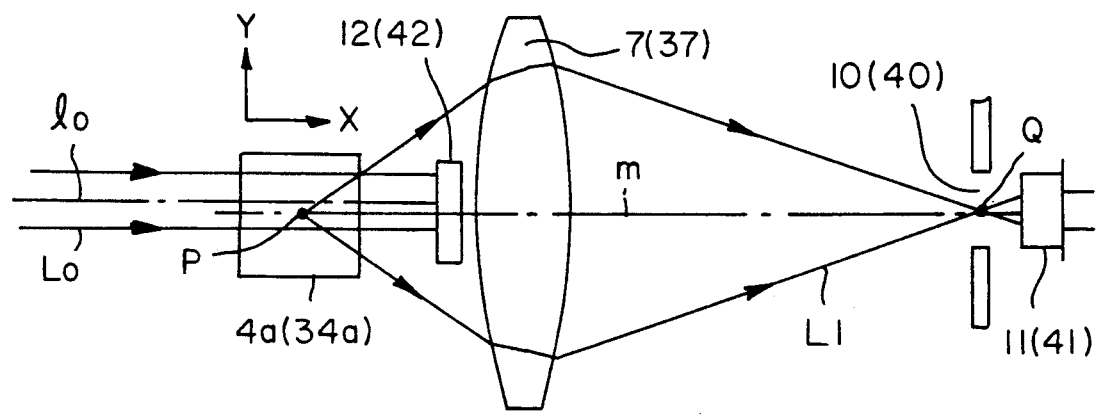
Figure 3B:
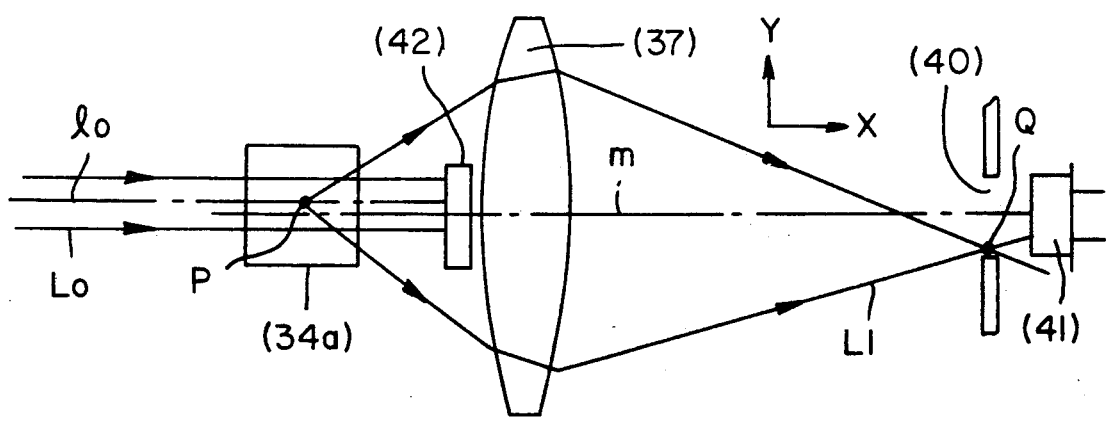
Figure 3C:
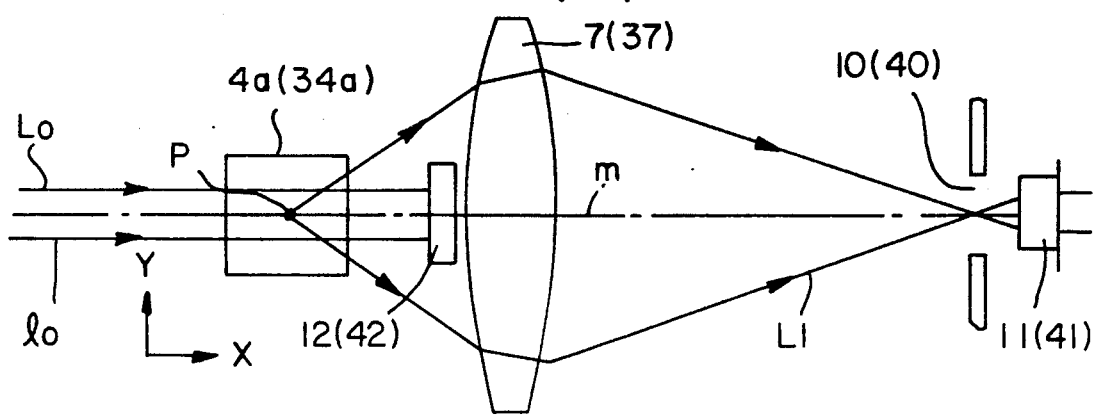
Figure 4:
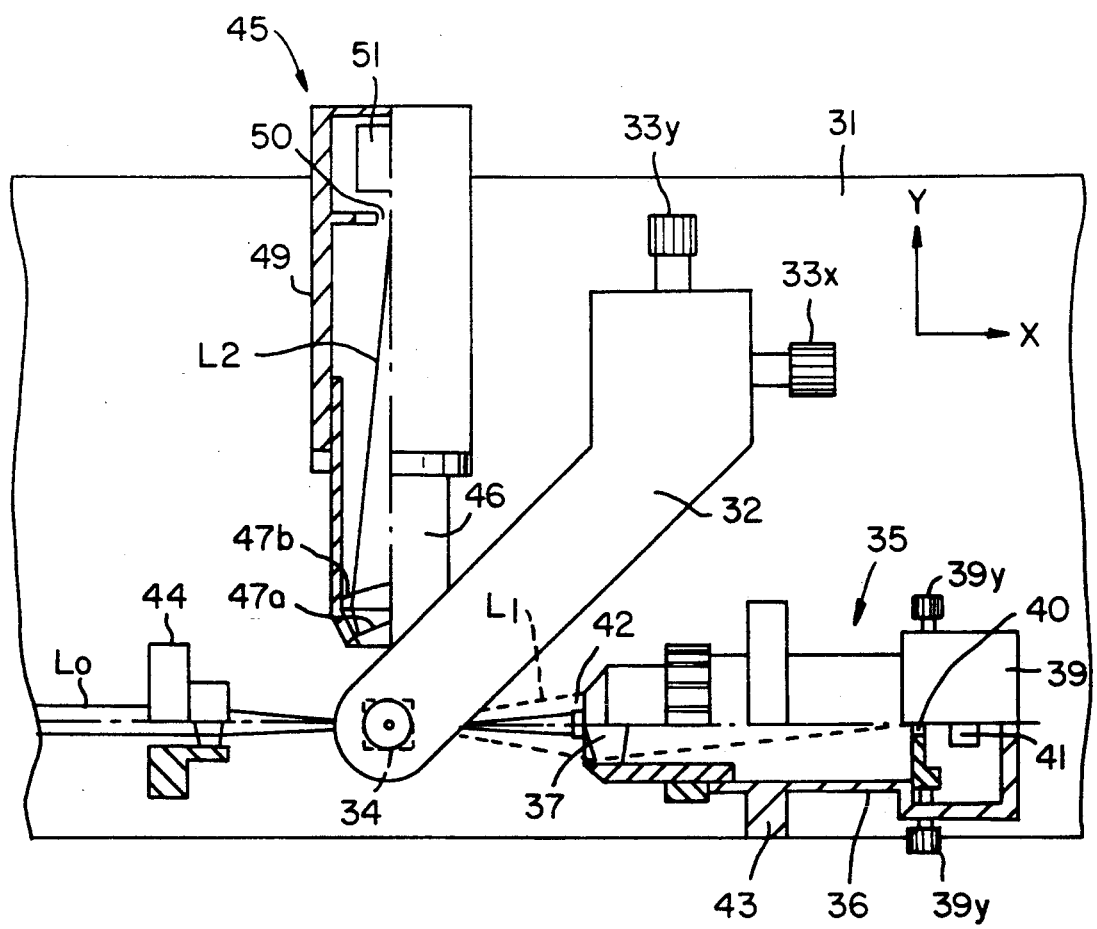
FIG. 4 is a plan view of a conventional flow cytometer, a part of which is a cross section to illustrate an optical portion of this conventional flow cytometer.
Figure 5:
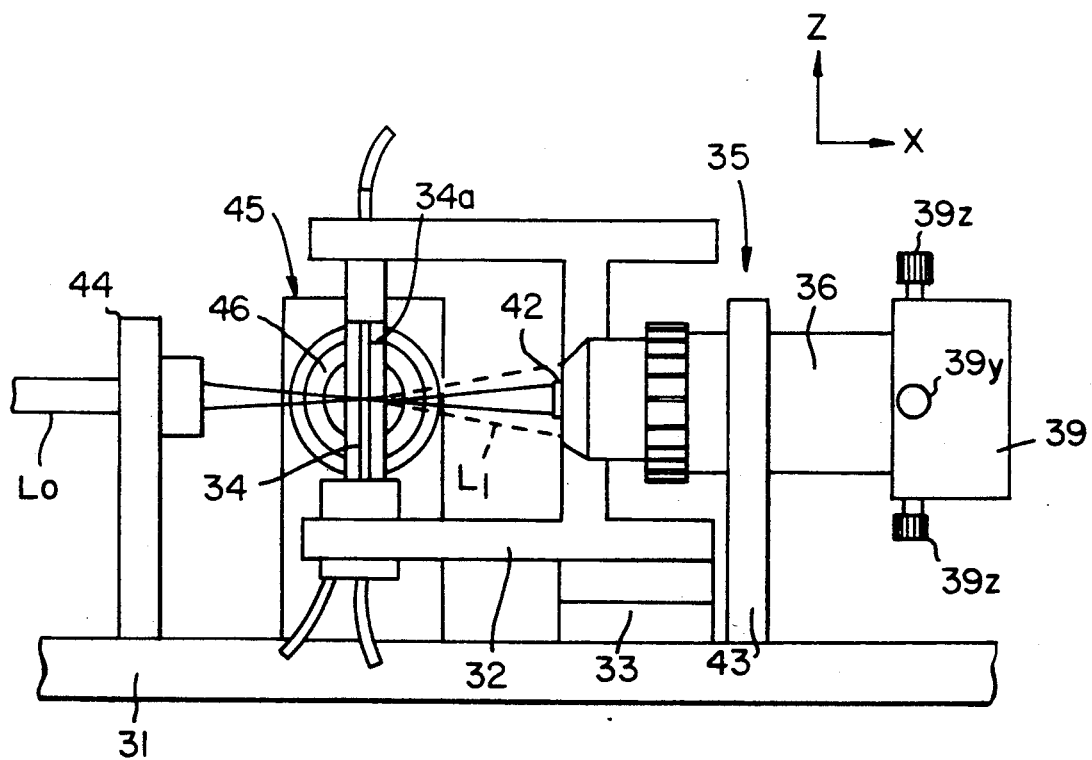
FIG. 5 is a side view of the optical portion of FIG. 4.

Referring to FIGS. 1, 2, and 3, FIG. 1 shows a plan view of the present flow cytometer, FIG. 2 is a side view of the optical portion, and FIGS. 3a, 3b, and 3c are common both to the prior art as well as to this invention.

FIG. 1, show a bench 1 for the flow cytometer on which mount 2 and right angle light detecting assembly 15 are disposed. Mount 2 is attached to the bench through a common adjustment mechanism 3. The adjustment mechanism 3 can move mount 2 in either the x or y direction by rotating the adjustment screws 3x and 3y respectively. Mount 2 is U-shaped and is attached to flow cell 4 and forward scattered light detecting assembly 5. Flow cell 4 is transparent with respect to any given wavelength and is made of synthetic quartz which is not fluorescent material. Numberal 4a denotes a flow channel of flow cell 4 through which a sheath liquid flows upward. Numberal 4b denotes an inlet into which a sample containing particles is injected. Numberal 4c denotes a inlet for the sheath liquid which is injected and 4d is an outlet for the sheath liquid.

Forward scattered light detecting assembly 5 has light path tubes 6a and 6b, light collecting lens 7, forward scattering light detector 9, and so on. Light path tube 6b has collecting lens 7 for collecting forward scattered light L1. Lens 7 is shown as a single lens but can be designed to be used as a combination of lenses. Light path tube 6b is inserted into light path tube 6a, and the depth of insertion is adjusted by rotating forward focusing adjuster 8. Specifically, by rotating forward focusing adjuster 8, the desired focusing can be obtained. Pinhole 10 and forward scattered light detector 11 are accommodated in forward scattered light detector container 9. Pinhole 10 can be slightly moved integrally with detector 11, together in the y and z directions by rotating adjustment screws 9y and 9z respectively. Forward scattered light L1 is then collected by lens 7 and after having the background noise removed by pinhole 10, the light enters detector 11 and is converted into electronic signals.

Beam blocker 12 has one side adjacent to lens 7 and the other side facing flow cell 4. The beam blocker 12 prevents light beam L0 from entering light detector 11 after having penetrated flow cell 4. It is preferable to move the beam blocker 12 together with the location adjustment mechanism (not shown) of light beam L0.

Laser focusing lens portion 14 consists of mount 14a and laser focusing lens 14b thereon. Focusing lens 14b focuses on particles flowing through flow channel 4a. Right angle light detecting assembly 15 consists of light path tubes 16 and 19, lenses 17a and 17b, right angle light path tube 19, and so on. Lenses 17a and 17b are disposed on the tip of light path tube 16 and collect signal light L2 from the particles. The other end of light path tube 16 is inserted into light path tube 19, of which the insertion depths are adjustable by rotating right angle focusing adjuster 18. In light path tube 19, pinhole 20 and light detector 21 are provided. The light signals L2 collected through lenses 17a and 17b, after having the background noise removed by pinhole 20, are then converted into electronic signals at light detector 21.

Generally, flow cytometers are provided with a pumping unit for sheath liquid and a sample and a processing unit for processing output signals from light detectors 11 and 21 but these units are not material parts of this invention and are therefore not described since their design is well known to persons skilled in this art.

The following is a description of the light axis adjustment of the present flow cytometer as shown in FIG. 3a. In this condition, light axes lo and m are not in line with each other and a particle p is on light axis m where forward scattered light L1 scattered from the particle p enters into light detector 11.

In FIG. 3a, flow cell 4 is slightly moved in the y-axis plus direction by rotating adjustment screw 3y to locate a particle p on light axis lo. At this moment, forward scattered light detecting assembly 5 is also moved together with flow cell 4 in the y-axis plus direction so that the relative locational relationship between forward scattered light detecting assembly 5 and flow cell 4 will not be disturbed as shown in FIG. 3b. Thus, no separate adjustment of forward scattered light detecting assembly 5 is required.

As flow cell 4 approaches the y-axis plus direction and as a particle p approaches light axis lo, particle p receives more intense light and the output signal of light detector 11 is thereby increased. If flow cell 4 is moved to the y-axis minus direction, the particle p moves out of line with light axis lo and the light intensity received by particle p is reduced which thereby reduces the output signal of light detector 11. Accordingly, it can be easily detected if the flow cell 4 moves erroneously in the y-axis direction. FIG. 3c illustrates a condition in which light axis lo and m are in line with each other after adjusting the light axis as mentioned above. If the locational relationship between flow cell 4 and forward scattered light detecting assembly 5 is incorrect, adjustment is necessary to make forward scattered light L1 from particle p correctly enter the light detector 11 by rotating adjustment screws 9y and 9z.

Also, the adjustment of flow cell 4 with respect to the x-axis direction is accomplished by adjustment screw 3x. This adjustment is executed to make signal light L2 correctly enter into light detector 21. In this case, the adjustment is easily completed without breaking the locational relationship between flow cell 4 and forward scattered light detecting assembly 5.

As illustrated above, according to this invention, the flow cell and the forward scattering light detecting assembly are integrally attached to a mount which is supported on a bench through an adjustment mechanism. Thus, it is easier to adjust a light axis without the additional special skill in adjustment as is necessary for the conventional flow cytometer.

What is claimed is:

1. A flow cytometer comprising:
   a flow cell containing a flowing stream of a number of particles which flow one at a time in a straight line through a flow channel;
   a light radiating means for radiating light on the particles flowing through said flow cell;

a forward scattered light detecting means for detecting light radiated in the same direction as said radiating light;

a right angle light detecting means for detecting light radiated at a right angle with respect to the direction of said radiated light;

a mount containing said flow cell and said forward scattered light detector mounted integrally together; and an adjustment mechanism for moving said mount containing said flow cell and said forward scattered light detector in either of an x or a y direction, wherein said flow cell and said forward scattered light detector maintain their locational relationship after adjustment.

2. A flow cytometer according to claim 1, wherein said forward scattered light detecting means comprises means for combining particles which are injected through a first inlet and combine with a flowing stream of sheath liquid which is injected through a second inlet.

3. A flow cytometer according to claim 1, wherein said light radiating means comprises a laser device that radiates said light through a focusing lens, whereby said focusing lens focuses said light onto the particles flowing in the flow channel.

4. A flow cytometer according to claim 1, wherein said forward scattered light detecting means comprises a forward scattered light detecting assembly, which comprises a forward scattered light detector, light path tubes, a light collecting lens, a forward scattered light detector container, a forward focusing adjuster, a pinhole, adjustment screws, a beam blocker, said flow channel and said flow cell.

5. A flow cytometer according to claim 1, wherein said right angle light detecting means comprises a right angle light detecting assembly which comprises right angle light path tubes, right angle light collecting lenses, a right angle focusing adjuster, a right angle light collecting lens, a pinhole and a right angle light detector.

6. A flow cytometer according to claim 1, wherein said right angle light detecting means detects scattered light and fluorescent light.

7. A flow cytometer according to claim 1, wherein said light detected in said same direction as said radiating light is primarily scattered light.

8. A flow cytometer according to claim 1, wherein said adjusting means comprises an adjustment mechanism which comprises adjustment screws which move said mount containing said flow cell and said forward scattered light detecting assembly together in either an x or y direction.

9. A flow cytometer according to claim 1, wherein said flow cell is transparent with respect to any given wavelength and comprises synthetic quartz which is not fluorescent material.

10. A flow cytometer according to claim 1, wherein said mount is U-shaped and is attached to said flow cell and said forward scattered light detecting assembly.

11. A flow cytometer according to claim 1, wherein said flow cell and said forward scattered light detecting assembly can be adjusted integrally together thereby maintaining their locational relationship after adjustment.

* * * * *